US006669650B1

(12) United States Patent
Anker et al.

(10) Patent No.: US 6,669,650 B1
(45) Date of Patent: Dec. 30, 2003

(54) BREAST SELF-EXAMINATION PROMPTER DEVICE

(76) Inventors: Denise M. Anker, 10062 S. Wyecliff Dr., Highlands Ranch, CO (US) 80126; Marvin L. Odefey, 9623 S. Townsville Cir., Highlands Ranch, CO (US) 80126

( * ) Notice: Subject to any disclaimer, the term of this patent is extended or adjusted under 35 U.S.C. 154(b) by 63 days.

(21) Appl. No.: 10/132,859

(22) Filed: Apr. 24, 2002

Related U.S. Application Data

(60) Provisional application No. 60/288,348, filed on May 2, 2001.

(51) Int. Cl.[7] ................................................ A61B 5/00

(52) U.S. Cl. .................... 600/551; 128/920; 340/309.2; 368/12

(58) Field of Search ................................ 600/300, 301, 600/551, 549, 587; 128/920, 897; 340/573.1, 309.16, 309.2–309.9; 434/416, 262, 433; 368/10, 12, 28, 107–108, 291, 327; 315/169.3, 76, 359, 363

(56) References Cited

U.S. PATENT DOCUMENTS 5,207,582 A * 5/1993 Michelson .................. 434/416
5,293,098 A * 3/1994 Brownell ................. 315/169.3
5,524,101 A * 6/1996 Thorgersen et al. .......... 368/10
5,657,753 A * 8/1997 Jacober et al. .............. 600/551
6,575,903 B1 * 6/2003 Collins ....................... 600/300

OTHER PUBLICATIONS

Aladdin Communications, "pPatrol™ Instructions", Dec. 19, 2002, pp. 1–5, Copyright Oct. 2000.*

* cited by examiner

*Primary Examiner*—Max F. Hindenburg
*Assistant Examiner*—Michael Astorino
(74) *Attorney, Agent, or Firm*—Leyendecker Law Offices; Kurt Leyendecker

(57) ABSTRACT

A breast self-examination prompter device having the purpose of prompting a user to perform a routine breast self-examination is described. The device includes a "Start" for activating the device and selecting a time cycle. A motion sensor is used to detect if a person is located near the device and cause the device to alert the person that the selected time cycle has been completed. The device also includes a micro-controller that provides control logic, timer and power control circuitry. An audio/visual component comprising one or both of an indicator light and an audible alarm is provided to alert the person. When the timing interval has expired and the motion sensor detects a person's presence, the micro-controller activates the audio/visual component. Also, the device includes a "Exam Complete" button for stopping the device.

20 Claims, 1 Drawing Sheet

BREAST SELF-EXAMINATION PROMPTER DEVICE

This application is based on a provisional application filed on May 2, 2001, Ser. No. 60/288,348, by the subject inventors and having the same title, which is hereby incorporated in its entirety.

BACKGROUND OF THE INVENTION (a) Field of the Invention

This invention relates to a device used as a prompter of a user of the device to take steps to perform a self-examination of her body and more particularly, but not by way of limitation, to a self-examination prompter device used for alerting the user of the device it is time to examine her breasts in the interest of early detection of any irregularities, i.e. tumors occurring in the user's breast.

(b) Discussion of Prior Art

In U.S. Pat. No. 5,657,753 and U.S. Des. Pat. No. 377,832 to Jacober et al., a home Breast Self Examination system is disclosed which can be used in a shower for monthly exams. The system includes prompt signals which are predetermined and programmed into the system by the user based on a women's individual menstrual cycle. This type of self-examination system is based on a programmable timer which is regulated by the user and signaling the user that a desired timing interval has expired. In U.S. Pat. Nos. 5,494,442 to Hecht and 5,207,582 to Michelson, two different breast recording systems are described for manually recording information related to home self examinations. Also, U.S. Pat. No. 5,474,064 to Rohrberg discloses a breast floatation system for self-examination. None of the above mentioned patents disclose the unique features, structure, objects, simplicity and advantages of the subject invention for providing a breast self-examination prompter device to help a person in the early detection of a mass, tumor, or other irregularity in the breast.

Breast cancer is the most common cancer among women, other than skin cancer. It is the second leading cause of cancer death in women, after lung cancer. The American Cancer Society predicts several hundred thousand new cases of breast cancer each year with some forty thousand deaths resulting from the disease. Breast cancer also occurs in men, although much less often.

The earlier breast cancer is found, the better the chances for successful treatment. Because early breast cancer does not produce symptoms, it's important for all women to follow the guidelines for finding breast cancer early. These include the following:

1. A mammogram and a breast exam by a doctor or nurse (clinical breast examination) every year for women over the age of 40.
2. Between the ages of 20 and 39, women should have a clinical breast exam every 3 years
3. All women over 20 should do breast self-examination (BSE) every month.

Together, these methods offer the best chance of finding breast cancer early.

With the above in mind, when is the best time for a women to do a self breast examination? This is all dependent upon a woman's menstrual cycle. The average woman's cycle is 28 days. Day one of a woman's menstrual cycle being the first day of menstrual bleeding. The end of the cycle being the first day of the next menstrual cycle. It is recommended by the medical community that a woman conduct a breast self-examination about one week after the start of the menstrual cycle or in other words days 7–10. The timing is crucial as hormone levels in a woman's body are lower at this time. This means, a woman's breasts will be less tender and less swollen. Therefore, less discomfort for the woman then facilitates a more thorough and complete exam.

But all menstrual cycles are not created equal. Women and their menstrual cycles or lack of menstrual cycles are categorized below.

1. Women with "regular" or predictable menstrual cycles.
2. Women with "irregular" or unpredictable menstrual cycles. These women having sometimes no idea when the start of their next menstrual cycle might be.
3. Women using birth control pills. These women have menstrual cycles that are dictated by the hormones in the pills. These women experience regular menstrual cycles each being 28 days.
4. Women that have no menstrual cycle which can occur for a variety of reasons:
   A. Post Hysterectomy
   B. Post Menopause, "The Change"
   C. Hormone Therapy
   D. Pregnancy
   E. Vigorous or Excessive Exercise In an effort to facilitate the practice of monthly breast self examinations, the subject device described herein has taken into account all of the above scenarios.

Women with "regular" or predictable menstrual cycles will benefit from using the 7 day timer mode as described. On day one of the menstrual cycle, the start button is depressed and automatically 7 days later the device will prompt the woman, with an audible alarm and a flashing light, to do her breast self-examination.

Women with irregular or unpredictable menstrual cycles will benefit from using the 7 day timer as well. Even though irregular, when the menstrual cycle begins the woman can depress the start button and the device will prompt her to do the breast self-examination on day 7.

For the woman using birth control pins, the subject invention has a 28 day clock (or timer). These women have very predictable menstrual cycles every 28 days. Therefore, the invention prompts the woman to do her breast self-examination every 28 days. In this mode, it is not necessary to depress the start button. The clock will automatically time out every 28 days.

The subject invention described herein also offers a 30 day clock which prompts the user to do the breast self-examination every 30 days or once a month. This mode is for all those not experiencing menstrual cycles. It should be noted too that men can benefit from using this mode as well. Here again, in the 30 day mode, it is not necessary to depress the start button. The clock will automatically time out every 30 days.

In situations where individuals have very infrequent menstrual cycles, it may be deemed more important to do a regular monthly exam rather than waiting for the menstrual cycle to actually start and then doing the exam one week later.

SUMMARY OF THE INVENTION

In view of the foregoing, it is a primary objective of the subject invention to provide a prompter device to prompt a user of the device that it is time to conduct a breast self-examination on a routine or monthly basis. The prompter device can also be used as a reminder to the user for periodically doing a self-examination for other medical conditions that need to be monitored on a regular basis.

A feature of the prompter device is that the device can be set to accommodate individual uniqueness as it pertains to signaling the user of a timing interval of 7 days, 28 days or 30 days. Pressing of a button will allow the user to choose between the three settings. The device is designed for use by pre-menopausal women with regular or irregular cycles, women using birth control pills, and the various groups of women that experience no menstrual cycle as a result of post hysterectomy, post menopause, hormone therapy, pregnancy, and a vigorous or excessive exercise. Monthly breast self-examination for men would be included here as well.

Still another feature of the invention is that the device is adapted for use in a bathtub setting or a shower stall, thus encouraging the user to perform the breast self-examination while the body is wet as suggested by the medical community. Further, performing the breast self-examination while bathing or showering allows the user privacy and convenience.

The breast self-examination device includes a micro-controller timer capable of timing a timing interval of 7 days, 28 days or 30 days. The micro-controller may comprise a microprocessor. For women that experience regular or irregular menstrual cycles there is a 7 day timer. For women using Birth Control Pills, there is a 28 day timer. For women who have non-menstrual cycles and men, there is a 30 day timer.

The breast self-examination prompter device also includes a motion sensor. The motion sensor is able to detect if a person is located near the breast self-examination device. The device also includes a micro-controller that serves multiple functions which includes the timer function, control logic and power control for the system, command for the motion sensor and audio/visual components. The micro-controller is connected to the motion sensor and an audio/visual circuit. The audio/visual circuit is made up of an indicator light and an audible alarm. When the timing interval has expired, then and only then, the motion sensor detects a person's presence, the micro-controller activates the indicator light and the audible alarm, whereby the user is reminded to perform a breast self-examination. If someone other than the intended user should activate the motion sensor, a "Not Me" button can be depressed, and the micro-controller/timer will continue uninterrupted. The audible alarm will sound for 30 seconds or until the "Exam Complete" button is depressed. If the intended user does not bathe or shower on a day the timer would normally expire, the audio/visual alarm will not activate but will recognize each successive day as an examination day as it awaits the intended user. If the "Exam Complete" button has not been depressed, the device will automatically continue uninterrupted until the end of the ongoing cycle.

The device also contains an energy saving circuit that distributes power to the motion sensor in pulses rather than in a continuous stream. Further, the micro-controller is designed to enter a "Sleep Mode" which shuts down all power except the power needed to operate its internal timer function.

These and other objects of the present invention will become apparent to those familiar with breast self-examination prompting devices used as an alert in prompting a breast self-examination when reviewing the following detailed description showing novel construction, combination and elements as herein described and more particularly defined in the claims. It being understood that changes in the embodiments to the herein disclosed invention are meant to be included as coming within the scope of the claims, except as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which.

DESCRIPTION OF THE PREFERRED EMBODIMENTS

Figure 1:
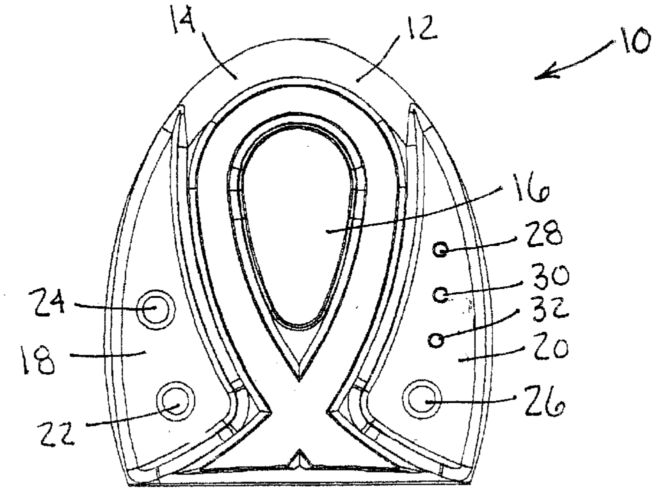
FIG. 1 is a front view of the subject breast self-examination prompter device being enclosed in a water-tight housing including with control buttons and motion sensor disposed behind a middle portion of the housing.

In FIG. 1, a front view of the subject breast self-examination prompter device is shown having a general reference numeral 10. The prompter device 10 is shown enclosed in a watertight housing 12 with electronics stored therein. The electronics are discussed under FIGS. 2 and 3. The housing 12 includes a top portion 14, a middle portion 16, a first side portion 18 and a second side portion 20.

The first side portion 18 of the housing 12 includes two control buttons. The buttons include an "Exam Complete" button 22 and a "Not Me" button 24 or a non-participatory button. The "Exam Complete" button 22, when depressed by the user signals to the device 10 that the user has completed a breast self-examination. Also, the "Exam Complete button 22 is used for turning the device "off". By depressing the "Not Me" button 24, the user signals to the device 10 that the person in the shower or bathtub is not intended person utilizing the device and the micro-controller with built-in timer continues uninterrupted.

On the second side portion 20 of the housing 12 is a "Start" button 26 wired to a seven day light 28, a twenty eight day light 30 and a thirty day light 32. When the "Start" button 26 is depressed by the user, the unit is turned "on". By depressing the "Start" button 26 only "once", the seven day light 28 is turned "on" and the device 10 is activated for a seven day timing cycle. This timing cycle is for achieving an optimal seven to ten day time period after the start of a women's menstrual cycle, in which a breast self-examination is recommended by the medical community. By depressing the "Start" button 26 "twice", the twenty eight day light 30 is turned "on" for a twenty eight day timing cycle. This timing cycle is recommended for women using birth control pills. By depressing the "Start" button 26 "three" times, the thirty day light 32 is turned "on" for a thirty day timing cycle. This timing cycle is for women who do not experience menstrual cycles and for use by men. It should be noted that when one of the selected lights 28, 30 or 32 is activated, the light will flash continuously at intervals of five to eight seconds.

Figure 2:
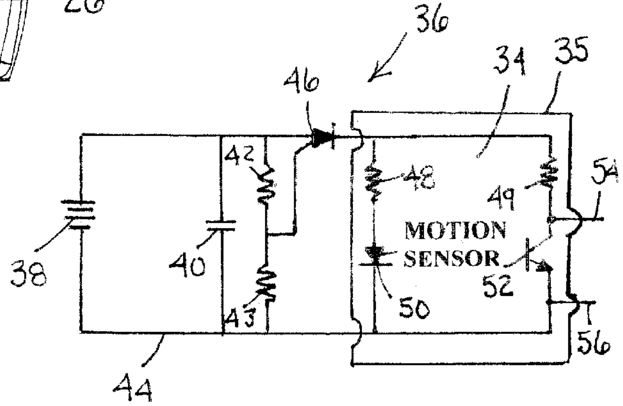
FIG. 2 is a schematic diagram of a unique power saving circuit developed to conserve power in a motion sensor portion of the device.
Figure 3:
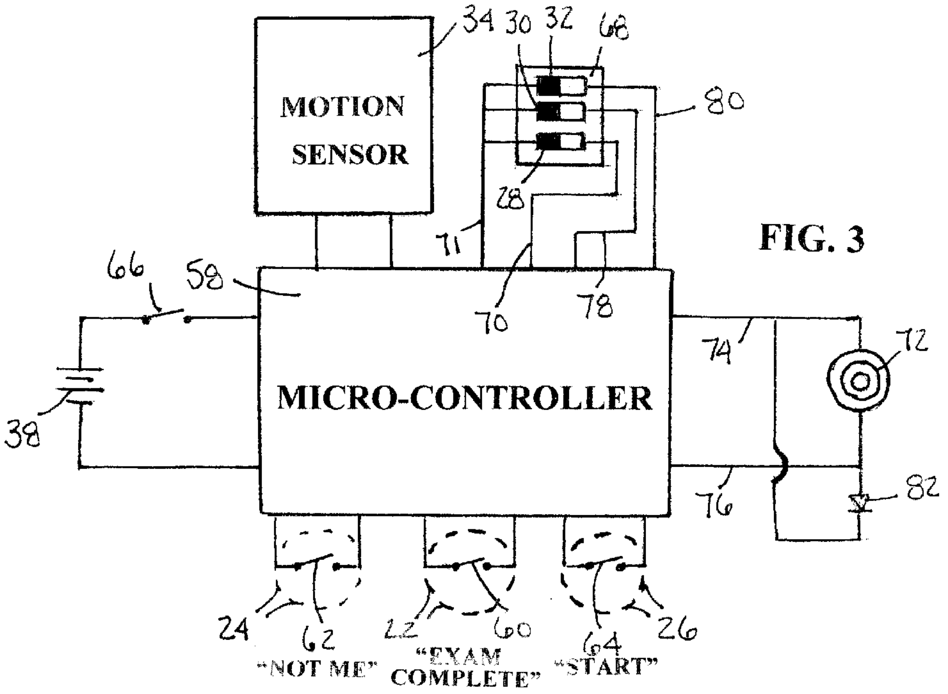
FIG. 3 is a block diagram of the breast self-examination prompter device that shows how the device processes all the information that is collected and generated.

Behind the middle portion 16 of the housing 12 is located a motion sensor 34 that may either be a pyro-electric or infrared system. The motion sensor 34 is shown in FIGS. 2 and 3. The motion sensor 34 is capable of detecting the presence of the user by emitting pulses of infrared energy that reflects off the entering person and is detected. In the case of the pyro-electric sensor, the heat of a person's body is detected.

In FIG. 2, a schematic diagram of a unique power saving motion sensor circuit is shown and having general reference numeral 36. The motion sensor circuit 36 is received inside the housing 12. The purpose of the motion sensor circuit 36 is to conserve the amount of power used by the motion sensor 34. The motion sensor 34 in this drawing is shown inside a box 35.

A Power is conserved in the circuit 36 by using a battery voltage power source 38 to ad charge up a capacitor 40 connected in an RC circuit 44 with resistors 42 and 43. Also, the capacitor 40 in the RC circuit 44 is connected to a unijunction transistor 46. Once power passes through the unijunction transistor 46, it enters the infrared motion sensor 34. The unijunction transistor 46 is a transistor that will allow no current to pass through it until the voltage across the transistor 46 reaches a critical point. This critical point is obtained as the voltage across the capacitor 40 is charged up.

Once the capacitor 40 reaches the critical voltage of the unijunction transistor 46, the stored energy of capacitor 40 is dumped across the transistor 46 into the infrared motion sensor 34, providing a pulse of power sufficiently long so as to allow the motion sensor 34 to sense motion. Thus, the unijunction transistor 46 acts as both a timer and a switch for the infrared motion sensor 34.

The amount of time it takes the capacitor 40 to charge to the critical voltage is controlled by a value of resistance for the resistors 42 and 43 in the RC circuit 44. The amount of energy release across the unijunction transistor 46 is dependent on the size of the capacitor 40.

The motion sensor 34 includes a resistors 48 and 49, an infrared emitter 50 and an infrared detector 52. The motion sensor 34 also includes electrical leads 54 and 56 for connecting the motion sensor to a micro-controller, which is shown in FIG. 3.

In FIG. 3, an overall electrical circuit schematic of the breast self-examination prompter device 10 is shown. As mentioned above, the prompter device is started when the user pushes the "Start" button 26 and a particular timing cycle is selected.

The electrical circuit of the prompter device 10 not only includes the motion sensor circuit 36, motion sensor 34 and battery voltage power source 38 shown in FIG. 2, but also a programmed micro-controller 58.

The micro-controller 58 is connected to the "Exam Complete" button 22, shown in dashed lines with an internal switch 60, the "Not Me" button 24, shown in dashed lines with an internal switch 62, and the "Start" button 26, shown in dashed lines with an internal switch 64.

As mentioned above, when the "Start" button 26 is pushed "once", the power source 38 closes a power switch 66 and the micro-controller 58 is activated and the motion sensor 34 is "on". Also, a switch/relay 68 is activated via electrical lead 70 and a return electrical lead 71 and the LED seven day light 28 is turned "on". Also, the micro-controller 58 is programmed to activate and sound an audio alarm 72 via electrical leads 74 and 76, when both the seven day cycle is complete and the motion sensor is triggered. The audio alarm 72 can be a buzzer or any similar sounding device. Also, the device 10 can include an optional visual alarm 82, which operates in conjunction with the audio alarm 72 and is connected to the leads 74 and 76 for sending a signal to the user when the selected cycle is completed.

If the "Start" button 26 is pushed "twice", the switch/relay 68 is activated via electrical lead 78 and the LED twenty eight day light 30 is turned "on" and the audio alarm 72 is sounded when the twenty eight day period is completed and the motion sensor is triggered.

Likewise, when the "Start" button 26 is pushed free times", the switch/relay 68 is activated via electrical lead 80 and the LED thirty day light 32 is turned "on" and the audio alarm 72 is sounded when the thirty day cycle is completed and the motion sensor is triggered. When motion sensor 34 senses motion in the shower or bath tub, then the motion sensor circuit 36 sends this information to the micro-controller 58 and it is processed. When the timing is complete for a selected cycle, the micro-controller 58 enables the audio alarm 72 and the alarm is sounded only when the motion sensor is triggered. At this time, the alarm 72 is energized for thirty seconds and will repeat every time the motion sensor 34 senses motion in the shower or bathtub until the "Exam Complete" button 22 is depressed.

If the user entering the shower or bath tub is not the intended user, this person depresses the "NOT ME" button 24. At this time the micro-controller 58 is programmed to shut "off" the power to the alarm 72, but the micro-controller 58 continues to operate uninterrupted.

When the alarm is received by the intended user, the audio alarm 72 is turned "off" by depressing the "Exam Complete" button 22. The user then conducts a breast self-examination. When the examination is complete, the subject self-examination prompter device 10 is now ready to be started again by pushing the "Star" button 26 one for the seven day mode. The twenty eight day mode and the thirty day mode restart automatically after the cycle is completed.

It is important to note that while the above discussion of the subject prompter device is centered around the prompting of a breast self-examination, it is appreciated that the prompter device 10 can be used equally well by the user in checking for other medical conditions and without departing from the spirit and scope of the invention as described herein. For example, the other types of medical conditions, but not limited to, could be regularly checking for possible testicle cancer, checking moles that may be pre-cancerous, checking for tumors and checking other irregularities that might have formed on the person's body. Also, it can be used for scheduled blood testing and injections.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. A self-examination prompter device for the purpose of prompting a user to perform a self-examination on a regular basis, the self-examination prompter device comprising:

a housing with a first switch for starting a first time interval;

a micro-controller received inside said housing, said micro-controller keeping track of the first time interval;

a motion sensor received in said housing and connected to said micro-controller, said motion sensor capable of detecting the presence of the user;

an electrical circuit with a power source, said electrical circuit connected to said motion sensor, said micro-controller and said first switch; and an alarm connected to said electrical circuit, the alarm being adapted to first signal the user only after both (1) the first time interval has expired, and (2) the presence of the user is detected by the motion sensor.

2. The prompter device as described in claim 1 further including a first visual indicator for indicating the first time interval on said housing, the first visual indicator being connected to said electrical circuit.

3. A self-examination prompter device for the purpose of prompting a user to perform a self-examination on a regular basis, the self-examination prompter device comprising:

a housing with a first switch for starting a first time interval;

a micro-controller received inside said housing, said micro-controller keeping track of the first time interval;

a motion sensor received in said housing and connected to said micro-controller, said motion sensor capable of detecting the presence of the user;

an electrical circuit with a power source, said electrical circuit connected to said motion sensor, said micro-controller and said first switch;

an alarm adapted to signal the user that the first time interval has expired, said alarm being connected to said electrical circuit;

a first visual indicator for indicating the first time interval on said housing, the first visual indicator being connected to said electrical circuit; and a second visual indicator for indicating a second time interval on said housing, the second visual indicator being connected to said electrical circuit, wherein said second time interval is a twenty eight day time interval and said first time interval is 7 days.

4. A self-examination prompter device for the purpose of prompting a user to perform a self-examination on a regular basis, the self-examination prompter device comprising:

a housing with a first switch for starting a first time interval;

a micro-controller received inside said housing, said micro-controller keeping track of the first time interval;

a motion sensor received in said housing and connected to said micro-controller, said motion sensor capable of detecting the presence of the user;

an electrical circuit with a power source, said electrical circuit connected to said motion sensor, said micro-controller and said first switch;

an alarm adapted to signal the user that the first time interval has expired, said alarm being connected to said electrical circuit;

a first visual indicator for indicating the first time interval on said housing, the first visual indicator being connected to said electrical circuit; and a second visual indicator for indicating a second time interval on said housing, the second visual indicator being connected to said electrical circuit, wherein said second time interval is a thirty day interval and said first time interval is 7 days.

5. The prompter device as described in claim 1 wherein said electrical circuit comprises an RC circuit with a uni-junction transistor.

6. The prompter device as described in claim 1 wherein said alarm includes an audible alarm.

7. The prompter device as described in claim 1 further including a second switch connected to said electrical circuit, the second switch adapted to turn off said alarm.

8. A breast self examination prompter device comprising:

a housing; and an electrical circuit at least partially within the housing, the electrical circuit including, (1) a motion sensor adapted to detect the presence of a person within proximity of the sensor;

(2) a first indicator; and (3) a micro-controller, the micro-controller is adapted in at least one operational mode to measure a first interval of time and activate the first indicator only after both (i) the first interval has passed, and (ii) the presence of the person is detected by the motion sensor.

9. The device of claim 8, wherein the electrical circuit further comprises one or more switches adapted to signal the micro-controller.

10. The device of claim 9, wherein the one or more switches are adapted to select the first interval of time from a plurality of time intervals.

11. The device of claim 9, wherein the one or more switches are adapted to deactivate the first indicator.

12. The device of claim 8, wherein the motion sensor comprises an infrared sensor assembly.

13. The device of claim 8, wherein the housing is substantially water tight.

14. A breast self examination prompter device comprising:

a housing; and an electrical circuit at least partially within the housing, the electrical circuit including, (1) a motion sensor adapted to detect the presence of a person within proximity of the sensor;

(2) a first indicator; and (3) a micro-controller, the micro-controller adapted to measure a first interval of time and activate the first indicator after (i) the first interval has passed, and (ii) the presence of the person is detected by the motion sensor; and wherein (a) the electrical circuit further comprises one or more switches adapted to signal the micro-controller, (b) the one or more switches are adapted to select the first interval of time from a plurality of time intervals, and (c) the plurality of time intervals also include a second interval of time, the first interval of time being about 7 days, and the second interval of time being one of about 28 days and about 30 days.

15. The device of claim 14, wherein the plurality of time intervals also include a third interval of time, the third interval of time being the other of about 28 days and about 30 days.

16. The prompter device of claim 9 wherein a first switch of the one or more switches comprises a button.

17. A device for prompting a person to perform a breast self-examination, the device comprising:

a motion sensor;

an alarm;

a micro-controller operatively coupled to the alarm and the motion sensor, the micro-controller adapted to (1) measure a predetermined first span of time, (2) measure a second span of time beginning substantially immediately after the first span of time has passed, and (3) activate the alarm after (i) the first span of time has passed, and (ii) the presence of the person is detected by the motion sensor before the second span of time passes, the second span being shorter than the first span.

18. A device for prompting a person to perform a breast self-examination, the device comprising:

a motion sensor;

an alarm;

a micro-controller operatively coupled to the alarm and the motion sensor, the micro-controller adapted to (1) measure a predetermined first span of time, (2) measuring a second span of time beginning after the fist span of time has passed, and (3) activate the alarm after (i) the first span of time has passed, and (ii) the presence of the person is detected by the motion sensor before the second span of time passes, the second span being shorter than the first span; and wherein the first span is one of about seven days, about 28 days and about 30 days, and the second span is about five days.

19. The device of claim 17, wherein the micro-controller is further adapted to measure successive time intervals of the first span of time and activate the alarm within the second span of time after a time interval of the successive time intervals has passed if the presence of the person is detected by the motion sensor.

20. The device of claim 17 further including one or more switches, the one or more switches being operatively coupled with the micro-controller, and being actuatable by the person to select the first time span from a set of different time spans.

* * * * *